United States Patent [19]
Benthin

[11] 4,367,734
[45] Jan. 11, 1983

[54] Y-FITTING IN THE PATIENT SYSTEM OF RESPIRATORS

[75] Inventor: Frank Benthin, Lübeck-Hamberge, Fed. Rep. of Germany

[73] Assignee: Drägerwerk Aktiengesellschaft, Fed. Rep. of Germany

[21] Appl. No.: 231,806

[22] Filed: Feb. 5, 1981

[30] Foreign Application Priority Data

Aug. 28, 1980 [DE] Fed. Rep. of Germany ....... 3032438

[51] Int. Cl.³ ............................................. A61M 11/04
[52] U.S. Cl. ................................ 128/204.13; 261/104; 261/DIG. 65
[58] Field of Search ....................... 128/200.11, 200.13, 128/203.12, 203.26, 203.27, 204.13, 204.17, 201.13; 261/104, DIG. 65

[56] References Cited

U.S. PATENT DOCUMENTS

| 2,067,120 | 1/1937 | George | 128/204.13 |
| 3,912,795 | 10/1975 | Jackson | 128/203.12 |
| 4,090,513 | 5/1978 | Towaga | 128/204.13 |
| 4,200,094 | 4/1980 | Gedeon et al. | 128/201.13 |
| 4,318,398 | 3/1982 | Oetjen et al. | 128/201.13 |

FOREIGN PATENT DOCUMENTS

| 2263720 | 7/1973 | Fed. Rep. of Germany | 128/203.26 |
| 2311558 | 12/1976 | France | 128/204.13 |
| 1294808 | 11/1972 | United Kingdom | 128/203.27 |

*Primary Examiner*—Henry J. Recla
*Attorney, Agent, or Firm*—McGlew and Tuttle

[57] ABSTRACT

An improved Y-fitting for the patient system of a respirator includes a membrane humidifier received therein and accommodating an exchangeable element including hollow filaments to which breathing air is directed and which are externally charged with water circulating therearound.

4 Claims, 2 Drawing Figures

Y-FITTING IN THE PATIENT SYSTEM OF RESPIRATORS

FIELD AND BACKGROUND OF THE INVENTION

This invention relates to respirators in general and, more particularly, to a Y-fitting in the patient system of respirators, in which a membrane humidifier is mounted within a housing. The membrane humidifier includes an exchangeable element and a plurality of hollow filaments for the passage of breathing air therethrough and means for externally charging the filaments with water circulating therearound.

A patient is connected to a respirator by means of an inspiration line and an expiration line. In a Y-fitting, the inspiration line through which the breathing gas is supplied is split up into a first branch leading to the patient, and a second branch leading, through a control valve, to the exhaling valve or, in a circulatory respirator, back to the circuit. With the control valve closed, the entire amount of breathing air flows through the first branch to the patient. With the control valve open, the breathing gas stream is deflected in the Y-fitting and, admixed to the air which is exhaled by the patient through the first branch, flows to the exhaling valve or returns to the circuit. By opening and closing the control valve, the breathing phases, the respiratory frequency and the ratio of inhalation to exhalation periods are controlled. Thus, the Y-fitting is an essential, indispensible component part of systems conducting breathing air.

In order to provide for the physical comfort of a patient, a satisfactory relative humidity of the breathing air is needed. A humidity level which is too low would dry up the respiratory tract. Therefore, breathing gas systems contain air dampeners or humidifiers.

Known humidifiers comprise a bundle of hollow filaments through which the breathing gas is directed. The filaments extend in axially parallel arrangement within a casing interposed in the system and provided with connections. The walls of the hollow filaments are impervious to water, but permeable to water vapor. At their front sides, the filaments are firmly connected to each other and to the inside of the casing by a sealing compound. Parallel to and within the bundle of filaments, a perforated tube for circulating water is also secured by the sealing compound. The supplied water flows around the hollow filaments and water vapor penetrates through the filament walls to their interior, thereby, humidifying the breathing air flowing therethrough. The provision of a humidifier in the breathing air supply way, particularly close to the patient as needed, results in a bulky arrangement (West German Pat. No. 26 17 985).

In another known humidifier, also designed with a bundle of hollow filaments inserted between the inspiration tube and a leg of the Y-fitting (European Offenlegungsschrift No. 00 09 543), the same problems as noted above arise.

SUMMARY OF THE INVENTION

The present invention is directed to an arrangement in which the breathing air humidifier is disposed in the patient section of the respiratory system, and which is optimal with respect to space utilization and handling, and preserves the security of the breathing system.

In accordance with the invention, there is provided a Y-fitting for the patient system of a respirator, which includes a housing, a membrane humidifier mounted within the housing, the membrane humidifier including an exchangeable element and a plurality of hollow filaments for the passage of breathing air therethrough, and means for externally charging the filaments with water circulating therearound.

Accordingly, it is an object of the invention to provide a respirator Y-fitting comprising a housing having a first housing section and a second housing section detachably mounted to the first housing section. The two sections define a compartment extending therethrough permitting flow of a breathing gas into a first connection of the first housing section and out through a second connection of the second housing section. The second housing section has a third connection communicating with the second connection permitting passage of expiratory air into the second connection and out through the third connection. A membrane element is removably mounted in the compartment and includes an outer tube and a plurality of hollow filaments mounted within the outer tube and extending across the compartment from the first connection to the second and third connections. The filaments are impervious to water and permeable to water vapor. The housing includes means for passing a flow of water about the filaments within the outer tube.

The advantages obtained with this design are due to combining two of the essential constructional elements into a single part which, in the past, were disposed in a manner requiring an excessive volume. Incorporation into the system is thereby simplified and, in addition, one coupling point is saved. This is a very important safety measure in artificial respiratory devices. A re-equipment of existing respiratory systems with humidifiers is thereby made substantially easier since re-equipment is reduced to the exchange of the Y-fitting. In addition, the heat radiation which must be controlled in connection with the dampening of the breathing gas is also reduced. The provided design of the housing permits a simple exchange of the used damping element.

In accordance with a preferred embodiment of the invention, a heat sensor is disposed in close proximity to the humidifier and the temperature can be controlled without influence from the outside.

A further object of the present invention is to provide a respirator Y-fitting which is simple in design, rugged in construction and economical to manufacture.

The various features of novelty which characterize the invention are pointed out with particularity in the claims annexed to and forming a part of this disclosure. For an understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figures 1, 2:
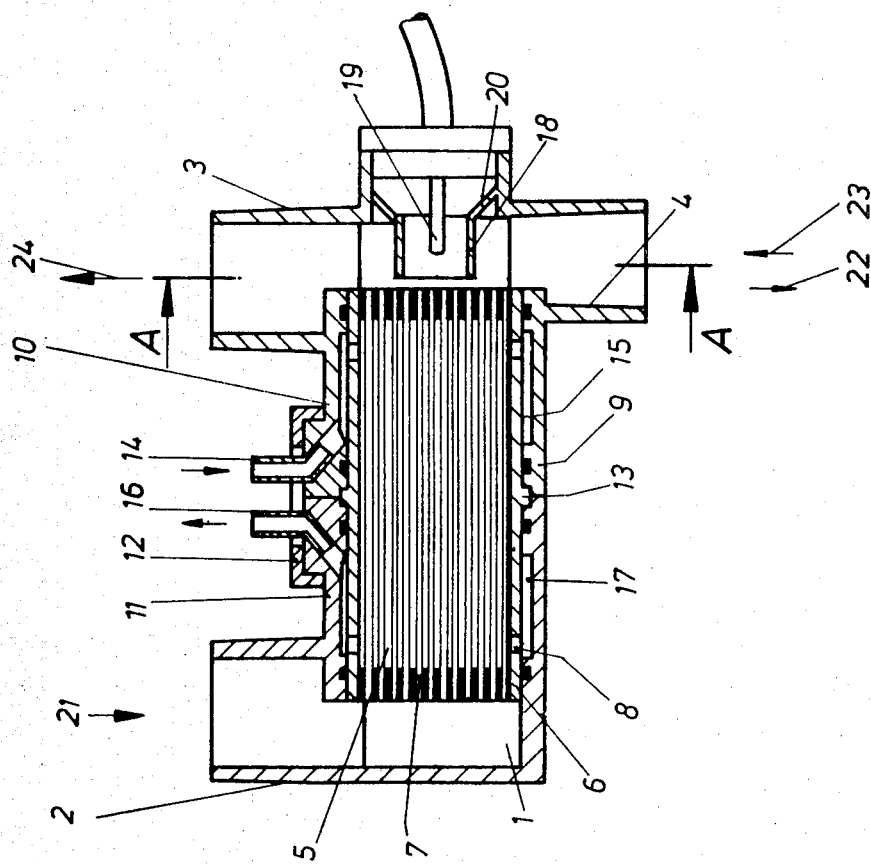
FIG. 1 is a longitudinal sectional view of a Y-fitting united with the breathing air humidifier.
FIG. 2 is a section taken along the line A—A of FIG. 1.

In a conventional Y-fitting, the inspiration line through which the breathing gas is supplied splits up into a first branch leading directly to the patient, and a second branch leading to the exhaling valve or back to the respiratory circuit. At the branching point, the air exhaled during the expiration period mixes with the breathing air which might still flow in through the inspiration line.

This known Y-fitting is replaced by the inventive Y-fitting united with an air humidifier 1. The fitting is composed of a housing 9 having a first housing part 11 and a second housing part 10, a first externally tapered connection 2 for the flexible inspiration tube of the patient's section of the system, an externally tapered connection 3 for the flexible expiration tube, and an internally tapered connection 4 for the flexible tube leading to the patient.

The air humidifier includes an outer tube 6 accommodating an exchangeable element 5 in which a bundle of hollow filaments 7 of a material impervious to water but permeable to water vapor is provided. Outer tube 6 is provided with apertures 8 through which water used for the dampening process is circulated. First and second housing parts 11, 10 are held in assembled state by a ring 12. If an exchange of element 5 is desired, ring 12 is removed; housing parts 10, 11 can then be removed from element 5. A new element 5 is inserted up to a stop shoulder 13 of one or the other of parts 10, 11. Upon fitting the other part thereto, housing 9 is again assembled and held in this state by ring 12.

To circulate the water, second housing part 10 is provided with a second or inlet connection 14 opening into a second recessed portion 15, and first housing part 11 is provided with a first recessed portion 17 and a first or outlet connection 16.

To dampen the breathing gas which is supplied in the direction of arrow 21 through hollow filaments 7 and internally tapered connection 4 in the direction of arrow 22 to a patient, a somewhat heated water flow is directed through second connection 14 into housing 9 and through second recessed portion 15 and apertures 8 to the bundle of hollow filaments 7 to flow therearound. The water which has not penetrated in the form of water vapor through the walls of the hollow filaments and been absorbed by the breathing gas, leaves housing 9 through first recess portion 17 and first connection 16. The branching zone between second externally tapered connection 3 and internally tapered connection 4 accommodates an open length of tube 18 in which a heat sensor 19 is disposed by means of which the temperature of the breathing gas leaving hollow filaments 7 is determined. To avoid obstruction of the breathing gas flow, tube 18 is held in position in housing 9 by means of supports 20. The exhaled air flows in the direction of arrow 23 through internally tapered connection 4 and then in the direction of arrow 24 out of the Y-fitting united with the humidifier 1.

Thus, in accordance with the invention, a Y-fitting in the patient system of respirators is characterized in that the fitting is formed by the housing 9 of a membrane humidifier which is received therein and accommodates an exchangeable element 5 including hollow filaments 7 through which breathing air is directed and which are externally charged with water circulating therearound. The housing 9 comprises a first housing part including a first externally tapered connection 2 for the flexible inspiration tube, and a second housing part 10 including an internally tapered connection 4 for the flexible tube connecting the patient thereto, and second externally tapered connection 3 for the flexible expiration tube and communicating with the internally tapered connection, with the two housing parts being held in assembled state by a detachable ring 12, and with the water being circulated through a second tube connection 14 and a second recess portion 15 in the second housing part 10 and through apertures 8 in the outer tube 6 of the element 5 back through a first recessed portion 17 and a first tube connection 16 of the first housing part 11. In the transition zone between the internally tapered connection 4 and the second externally tapered connection 3, the second housing part 10 accommodates a heat sensor 19 which is disposed in an open tube length 18 connected to the second housing part 10 by supports 20.

While a specific embodiment of the invention has been shown and described in detail to illustrate the application of the principles of the invention, it will be understood that the invention may be embodied otherwise without departing from such principles.

What is claimed is:

1. A Y-fitting for the patient system of a respirator, comprising, a housing, a membrane humidifier mounted within said housing, said membrane humidifier including an exchangeable element with a plurality of water vapor permeable hollow filaments and mounting means for mounting said filaments in side-by-side and spaced relationship in said element thereby defining a flow path for breathing gas therethrough and a water space therearound and means supplying water to said water space for externally charging said filaments with water circulating therearound, said housing comprises a first housing part including a first externally tapered connection for receiving a flexible inspiration tube and means for surrounding and sealably securing one end of said exchanged element therein providing a gas flow path between said first externally tapered connection and said filaments, a second housing part including an internally tapered connection for receiving a flexible tube connecting to the patient and a second externally tapered connection for receiving a flexible expiration tube and communicating with said internally tapered connection and means for surrounding and sealably securing the opposite end of said exchangeable element therein providing a gas flow path between said filaments and said internally tapered connection and said second externally tapered connection, a ring detachably connecting said first housing part to said second housing part, said first housing part having a first tube connection and a first recess portion surrounding said exchangeable element and communicating with said first tube connection, said second housing part having a second tube connection and a second recess portion surrounding said exchangeable element and communicating with said second tube connection and passage means in said mounting means communicating with said first and second recess portions whereby water is circulated from said first tube connection and recess portion through said space and back through said second recess portion and said second tube connection of said second houging part.

2. The Y-fitting, according to claim 1, further comprising an open tube and a heat sensor mounted in said open tube, said open tube being mounted to said second housing part intermediate said internally tapered connection and said second externally tapered connection.

3. A Y-fitting of a respirator for supplying humidified breathing air to a patient comprising:

a housing defining a humidifier compartment and including a first housing part for defining a first portion of said humidifier compartment, said first housing part having a first connection for receiving a flexible inspiration tube, said housing including a second housing part for defining a remainder of said humidifier compartment and including a second connection for receiving a flexible expiration tube, said second housing part including a further connection for receiving a flexible tube adapted to be connected to a patient, said second and further connections being in fluidic communication with each other and extending on opposite sides of said housing part;

removable engagement means connected to said first and second housing parts for holding said first and second housing parts together to define said humidifier compartment;

an exchangeable membrane humidifier element comprising a plurality of water vapor permeable hollow filaments and mounting means for mounting said filaments in side-by-side and spaced relationship in said element thereby defining a flow path for breathing air from said first connection, through said filaments and to said second and further connections and defining between said filaments a water receiving space, said housing including means for sealingly securing said mounting means in said compartment;

said first housing part including a first recess communicating with said compartment and defining together with said mounting means a first channel, said mounting means having first passage means fluidically connecting said water space with said first channel;

said second housing part including a second recess communicating with said compartment and defining together with said mounting means a second channel, said mounting means having second passage means fluidically connecting said water space with said second channel;

a first water receiving tube connection connected to said first housing part and communicating with said first channel; and a second water receiving tube connection connected to said second housing part and communicating with said second channel;

whereby water supplied to one of said tube connections circulated in said space around said filaments to humidify air passing through said filaments and thereafter exits from said space through the other tube connection.

4. A Y-fitting according to claim 3, including an open ended tube connected to said second housing part and extending into a space between said second and further connections, and a heat sensor mounted in said open tube.

* * * * *